(12) United States Patent  
Chornenky et al.

(10) Patent No.: US 11,129,999 B2  
(45) Date of Patent: Sep. 28, 2021

(54) THERMALLY ASSISTED PULSED ELECTRO-MAGNETIC FIELD STIMULATION APPARATUS AND METHOD FOR TREATMENT OF OSTEOARTHRITIS OF THE KNEE

(71) Applicant: Minnesota Medical Physics LLC, Eden Prairie, MN (US)

(72) Inventors: Victor I. Chornenky, Minnetonka, MN (US); Ali Jaafar, Eden Prairie, MN (US)

(73) Assignee: Minnesota Medical Physics LLC, Eden Prairie, MN (US)

(*) Notice: Subject to any disclaimer, the term of this patent is extended or adjusted under 35 U.S.C. 154(b) by 321 days.

(21) Appl. No.: 16/261,499

(22) Filed: Jan. 29, 2019

(65) Prior Publication Data

US 2020/0238098 A1  Jul. 30, 2020

(51) Int. Cl.
*A61N 2/00* (2006.01)
*A61N 2/02* (2006.01)
*A61N 1/40* (2006.01)
*A61F 7/00* (2006.01)

(52) U.S. Cl.
CPC .......... *A61N 2/008* (2013.01); *A61N 2/002* (2013.01); *A61N 2/02* (2013.01); *A61F 2007/0042* (2013.01); *A61N 1/40* (2013.01)

(58) Field of Classification Search
None
See application file for complete search history.

(56) References Cited

U.S. PATENT DOCUMENTS

| | | | | |
|---|---|---|---|---|
| 6,179,772 B1 * | 1/2001 | Blackwell | ................ | A61N 2/02 600/13 |
| 8,932,196 B2 * | 1/2015 | Chornenky | .............. | A61N 2/02 600/14 |

* cited by examiner

*Primary Examiner* — Michael W Kahelin

(74) *Attorney, Agent, or Firm* — Skaar Ulbrich Macari, P.A.

(57) ABSTRACT

A method, apparatus and a system for thermally-assisted pulsed electromagnetic field stimulation for treatment of osteoarthritis in the knee are disclosed. A multi-coil applicator is adapted for positioning around the knee. A first coil is positioned on the top of the knee and provides electric field stimulation in the plane of the patella to stimulate the patella cartilage. Second and third coils are rectangular coils wrapped up below and above the knee respectively. The coils in the wrapped position generate a magnetic field along the knee axis and provide high amplitude of the electric field stimulation of the femoral and tibial cartilages in the plane of tibial plateau. Resistive heaters and free wheel diodes can be provided to the applicator to supply uniform thermal stimulation around the knee joint.

21 Claims, 7 Drawing Sheets

THERMALLY ASSISTED PULSED ELECTRO-MAGNETIC FIELD STIMULATION APPARATUS AND METHOD FOR TREATMENT OF OSTEOARTHRITIS OF THE KNEE

FIELD

The invention relates to a method and apparatus for pain management, anti-inflammation and treatment of osteoarthritis of the knee. More particularly, the invention relates to an apparatus and method for producing pulsed electromagnetic field in the cartilage of an osteoarthritic knee for activation of adenosine—A2AR anti-inflammatory pathway in combination with thermal stimulation.

BACKGROUND

Osteoarthritis (OA), sometimes called degenerative joint disease, is a chronic disorder associated with damage to the articular cartilage and surrounding tissues and characterized by pain, stiffness and loss of function. OA commonly affects the hands, spine, and large weight-bearing joints, such as the hips and knees. OA affects nearly 21 million people in the United States, accounting for 25% of visits to primary care physicians. Eighty percent of the U.S. population has radiographic evidence of OA by age 65, and 60% of those are symptomatic. In the United States, hospitalizations for osteoarthritis soared from 322,000 in 1993 to 735,000 in 2006.

Articular cartilage is the smooth white tissue that covers the surface of all the synovial joints in the human body. Its main function is to facilitate the movement of one bone against another. With the coefficient of friction as low as 0.003 and the ability to bear compressive loads as high as 20 MPa, articular cartilage is ideally suited for placement in joints, such as the knee and hip. Articular cartilage is composed mainly of water (70-80% by wet weight). It contains specialized cells called chondrocytes that produce a large amount of extracellular matrix composed of collagen, chondroitin and keratan sulfate proteoglycan. Collagen forms a network of fibrils, which resists the swelling pressure generated by the proteoglycans, thus creating a swollen, hydrated tissue that resists compression. Cartilage is one of the few tissues in the body that does not have its own blood supply. For nutrition and release of waste products chondrocytes depend on diffusion helped by the pumping action generated by compression of the cartilage. Compared to other connective tissues, cartilage grows and repairs more slowly.

In addition to proteins and proteoglycans that comprise the extracellular matrix, the chondrocytes produce the enzymes causing degradation of the matrix. This way the chondrocytes maintain a permanent turnover and rejuvenation of the cartilage.

The chondrocytes and the cartilage matrix change with advancing age. The chondrocytes are responsible for both the production of new matrix proteins and the enzymes related to the cartilage degradation. It is generally accepted that the osteoarthritis process includes alterations in the normal balance between synthesis and degradation of articular cartilage and the subchondral bone. In younger individuals the chondrocytes are capable of the appropriate maintenance of the cartilage tissue and keeping it healthy and functional. But with advancing age, the chondrocytes become incapable of providing adequate repair and the process is tipped towards degeneration.

For many years healthy cartilage tissue not only preserves its integrity and function but also performs a constant remodeling to meet requirements of changing loads on the joints. Multiple regulatory pathways by which chondrocytes in articular cartilage sense and respond to the mechanical stimuli have been discovered in recent studies. One of the pathways is a mechanical one, in which the chondrocytes sense the pressure on the cartilage and respond by gene transcription, translation and post-translational modification of the extracellular matrix. Another pathway is a cellular response to the electrical signals generated by the loaded cartilage tissue. It was discovered that an electric potential appears on a cartilage tissue if it is mechanically stressed. It was shown also, that the electric signal on a loaded cartilage tissue can be produced by two physical phenomena: a piezoelectric effect and a streaming potential.

Piezoelectric effect is the ability of some materials to generate an electric field in response to applied mechanical stress. Piezoelectric effect has been observed in a number of soft and hard tissues (including cartilage and bone) and appears to be associated with the presence of oriented fibrous proteins such as collagen. A deformation of a protein molecule produces an asymmetric shift of the opposite electric charges comprising the molecule and results in a macroscopic electric potential on the stressed tissue.

A streaming potential is produced when a liquid is forced to flow through a capillary or porous solids (including cartilage and bone). The streaming potential results from the presence of an electrical double layer at the solid-liquid interface. This electrical double layer is made up of ions of one charge type which are fixed to the surface of the solid and an equal number of mobile ions of the opposite charge which are distributed through the neighboring region of the liquid phase. A mechanical stress applied to such a system creates a flow of the mobile ions with respect to the fixed ions on the solid which constitutes an electric current. The electric potential on the tissue generated by this current is called a streaming potential.

Whatever the relative contribution of these two mechanisms is to the electric signal on the stressed tissue, a substantial electric potential is created across the loaded cartilage. It has been suggested that this stress-generated potential (SGP) may play a significant role in cartilage growth, repair, and remodeling. Moreover, because SGP provides a link between physiology and physics it may open a new opportunity of influencing biological processes in the articular cartilage. It has been proven by numerous studies that an increase in chondrocytes cell division and the collagen and proteoglycan synthesis are possible and may be achieved in vivo by applying electric potential to the cartilage. This can be done with relatively simple medical devices. In the future these devices promise to become a new non-invasive modality of treatment of arthritis and other cartilage diseases.

Currently available treatment options for osteoarthritis focus on symptoms relief, whereas truly disease-modifying agents are lacking. Thus, the basic therapy includes common analgesics, non-steroidal anti-inflammatory drugs (NSAID), physical therapy and eventually, in severe cases, joint replacement surgery. Conventionally, physicians treat patients exhibiting symptomatic osteoarthritis by the administration of a NSAID. Many such non-steroidal anti-inflammatory drugs are known and are often effective in reducing the symptoms of osteoarthritis. NSAIDs have demonstrated ability to relieve pain, improve activity level, and in some cases improve function of the arthritic joints. None of these drugs, however, have been proven in carefully controlled clinical trials to reverse the long term natural history of osteoarthritis. Moreover, while many of these drugs have demonstrated effectiveness in treating the symptoms of osteoarthritis, they also have been associated with significant toxicities and other risks, such as deleterious effects on cartilage when used over prolonged periods of time. Moreover, in addition to NSAID being very expensive, the toxicities of these drugs limit their usefulness, particularly in elderly patients. Side effects from NSAIDs could be severe; they cause over 20,000 deaths annually in the U.S.

Appropriate exercises, including stretching, strengthening, and postural exercises help maintain healthy cartilage, increase joint's range of motion and strengthen surrounding muscles so that they can absorb stress better. Exercises can sometimes stop or even reverse osteoarthritis of the hips and knees.

Heat Therapy: Heat increases blood flow and makes connective tissue more flexible. It temporarily blocks pain, helps reduce inflammation, stiffness, and improves range of motion. Heat may be applied to the body surface or to deep tissues. Hot packs, infrared heat and hydrotherapy provide surface heat. Electric currents or ultrasound generate heat in deep tissues. Research shows that heat disrupts the body's usual pain cycle by stimulating heat sensors and preventing sensation of pain from reaching the brain. Because the cartilage tissue does not have its own pain receptors, sensation of pain in affected joints comes from underlying bones which are rich in pain receptors. Namely these receptors are blocked by the heat. As of today, there is no direct evidence that the heat therapy itself can reverse or even slow down degeneration of the cartilage affected by arthritis.

Pulsed Electromagnetic Field (PEMF) therapy has been known for several decades. It started from observations made by several researchers in the nineteen seventies that the pulsed magnetic field had a positive effect on healing bone fractures and damaged cartilage. At that time many researchers believed that the healing effect was produced by the magnetic field itself and many PEMF applicators with different temporal and spatial patterns of applied magnetic field were claimed as beneficial and patented. The differences between the patented features in the designs of the applicators and methods of treatment were in the amplitudes, lengths of magnetic pulses, their shapes, mainly rectangular and sinusoidal, repetition rates (frequencies), geometry and electrical parameters of the coils. Also, much effort and creativity were directed to the ergonomics of the PEMF applicators and methods of their positioning near or securing to the human body. It was perceived then that the most important therapeutic parameter of the system was the amplitude of the magnetic field, so the coils were built with high numbers of turns and pulsed magnetic fields up to hundreds of Gauss were generated.

Alternating electrical fields for the same purpose of bone fracture healing and treatment of damaged cartilage were exploited by several research groups in laboratory studies and clinical trials. Even though the electrical field applicators in these studies proved to be therapeutically effective they revealed a serious drawback—necessity to implant electrodes into the vicinity of the treatment area or at least apply electrodes from outside the body with electrically intimate contact to the skin. In comparison with the electrical systems the PEMF applicators have an advantage of not only being non invasive, but also not requiring an intimate electrical contact with the skin. Contrary to the electric field, magnetic field at the employed frequencies easily penetrates the human body practically to any depth.

In an electric field stimulation system developed by Brighton et al. (U.S. Pat. No. 7,158,835 B2 and others of the same inventor) a sinusoidal frequency of 60 kHz was employed. This relatively high frequency allowed achieving good capacitance coupling of the treatment volume of the joint with the electrodes at the skin adjacent to the joint. Clinical success of the 60 kHz system proved that the stimulating effect on the cartilage can be achieved with much higher frequencies then tens or hundreds of Hz. It can be expected that the therapeutic effect of the electric fields on cartilage and bone healing exists in a frequency range from a fraction of Hz to up to at least 60 kHz.

Now it is common knowledge among researchers that the active agent of the PEMF systems is the electric field. Namely electric field interacts with biological tissues, not the magnetic field. From general theory of electromagnetic field it is known that an electric field accompanies every change in time of the magnetic field. Being more specific, the electric field E, created by varying magnetic field, is directly proportional to the time derivative of the magnetic inductance B. The energy associated with the electric field also comes from the magnetic field. It should be noted that the electric field created by a changing magnetic field has one significant difference from the electric field created by electric charges at rest (electrostatic fields): it is a curly field, not potential as the field produced by the electric charges. Contrary to the potential field, in which the field lines begin on positive charges and terminate on the negative charges, the field lines of the curl electric field are continuous; they form closed loops, very much like the magnetic field lines around a wire with an electric current. This nature of the curly electric field imposes some limitations on the way the devices, whose intended use is the application of the electric field to human body, should be built. One of these limitations is the presence of areas with very low electric fields, "dead zones". The dead zones are located near the axes of the electromagnetic coils and produce no therapeutic effect on the treated tissue.

In U.S. Pat. No. 5,842,966 issued to Markoll a method for treatment of arthritis is disclosed. The method involves treating organs by applying a magnetic field by means of an annular coil surrounding the organ, the coil being energized by a pure DC voltage having a rectangular wave form pulsing at the rate of 1-30 CPS. The invention also includes an apparatus comprising a body support encompassed by an annular coil energized as above. The coil is mounted on a carriage running on tracks adjacent the body support. This disclosed device and method has a dead zone along the center axis of the coil.

In U.S. Pat. No. 7,158,835 B2 issued to Brighton et al., a PEMF device is disclosed for preventing and treating osteoporosis, hip and spine fractures, or spine fusions by incorporating a conductive coil into a garment adapted to be worn adjacent to a treatment area and applying an electrical signal to the coil to produce a magnetic flux that penetrates the treatment area and produces an electric field in the bones and the treatment area. The disclosed device has dead zones along the center axes of the coils. The device does not include any heating means.

In U.S. Pat. No. 6,701,185 issued to Burnett et al., an apparatus for electromagnetic stimulation of nerve, muscle, and body tissues is disclosed. The apparatus is comprised of a plurality of overlapping coils which are able to be independently energized in a predetermined sequence such that each coil will generate its own independent electromagnetic field and significantly increase the adjacent field. The coils are co-planar and are disposed in an ergonomic body wrap, which is properly marked to permit an unskilled patient to locate the body wrap on a particular part of their body so that the stimulation coils will maximize the electromagnetic stimulation on the selected nerves, muscles, and/or body tissues near the treated area. The device can be used to treat medical conditions including: muscular atrophy, neuropathic bladder and bowel, musculoskeletal pain, arthritis, as well as possible future applications in the prevention of deep vein thrombosis and weight reduction. This PEMF device has much more uniform electrical field than a simple coil and does not have dead zones. The device does not have a heating element and does not provide PEMF treatment at elevated temperatures.

In U.S. Pat. No. 6,179,772 issued to Blackwell a portable electronic PEMF apparatus is disclosed. The apparatus comprises a PEMF coil, power supply, and electronic switching means. The power supply along with the switching means provide periodic electric power to the PEMF coil. The PEMF coil comprises multiple turns of a conductive wire around a core. The core comprises a magnetic shield layer of materials such as mu metal or soft iron. The power supply comprises a battery, a regulated voltage source and unregulated voltage source from the battery and electronic switching circuit. The electronic switching circuit is tuned to periodically provide power to the coil at a frequency to generate a non-inverting, varying electromagnetic field from the coil. Disclosed apparatus also comprises a heating means. This heating means that provides heat to a body part under treatment is an electric resistive heater, or, in another implementation, a chemical heater. In both cases the applied heat is not regulated and the temperature of the treatment area is not controlled.

In U.S. Patent Application Pub. No. US 2008/0288035, by Jagjit et al., a stimulation device for treating osteoarthritis is disclosed. The device is intended for therapeutic treatment to a body part such as a joint to promote healing of the body part. It comprises a signal generator for generating a pulsed electromagnetic field based upon a selected treatment mode, a controller for storing the treatment mode and communicating the treatment mode to the signal generator, a heat source configured to provide thermal therapy to the body part, and monitoring means for monitoring the electromagnetic field generated by the electromagnetic stimulating means. The disclosed device uses a heat or cold source to block pain. The cold and heat sources, mainly chemical in nature, are not controlled by any means; they have drifting temperatures and do not provide PEMF therapy in the optimal range of temperatures for osteoarthritis treatment.

In U.S. Pat. No. 7,783,348, to Gill et al., a PEMF device for treatment of an arthritic knee joint is disclosed. The device comprises a knee cuff positionable around the knee, the electromagnetic stimulator comprising two coils on the right and left sides of the knee and two single use heaters secured at the left and the right sides of the knee inside the two coils and configured to provide temperature-based therapy to the knee joint. The Gill device suffers from several significant drawbacks. First, the coils generate magnetic field parallel to the cartilage layers between femoral and tibial bones and the layer of patella cartilage. Changing the magnetic field produces an electric field perpendicular to the cartilage layers crossing the adjacent bones in sequence with cartilage. The electrical resistivity of bones is several times higher than that of cartilage, so the electric field in the cartilage is several times lower than that in the adjacent bones. This leads to significant losses of therapeutic effects. Another drawback of the Gill device is that the thermal stimulation is highly non-uniform throughout the knee. The patella gets no stimulation at all and stays cold, whereas the femoral-tibial joint is thermally stimulated only in two small spots on the right and left sides of the knee, which comprise less than 10% of the whole surface of the knee.

A TA-PEMF system for treatment of osteoarthritis of the knee is disclosed in U.S. Pat. No. 8,460,167 B2 and U.S. Pat. No. 9,486,638, both to Chornenky et al. Though efficient and usable, this system suffers from a drawback that the disclosed knee applicator is designed in a shape of a stretchable tube (hose) with several electromagnetic coils incorporated into elastic fabric of the tube (hose). For treatment this applicator must be pulled by a user over the knee from the foot up. In the disclosed patent two coils are designed to provide PEMF in the direction along the knee. Patients that are overweight, elderly and/or fragile may experience difficulty placing the applicator and have significant discomfort with this disclosed configuration. U.S. Pat. No. 8,460,167 B2 and U.S. Pat. No. 9,486,638 are both hereby incorporated herein by reference in their entirety.

There is a need for an improved device and method for treating OA in the knee that remedy the drawbacks of the prior art treatment devices and methods.

SUMMARY

The present invention effectively addresses certain drawbacks in the prior art OA treatment devices and methods. One objective of certain embodiments of the present invention is to provide a more ergonomic knee PEMF applicator that is easier to use by all users including overweight, elderly and fragile patients. Another objective is to provide well controlled and uniformly distributed thermal stimulation of the knee joint.

In accordance with one aspect of certain embodiments of the invention, a knee applicator wraps around the knee with all coils, resistor heaters and free wheel diodes secured flat on the surface of the applicator wrap. Disposing two coils (a femoral and a tibial) around the knee creates two electric circuits that generate magnetic field along the knee normally to the tibial plateau. A third coil provided to the applicator is a flat coil (Tesla coil) and positioned over the knee cap. This third coil generates magnetic field normally to the patella. Sequentially changing the magnetic field generated by the coils provides an electric field stimulation of the cartilage in the plane of tibial plateau by the two coils and in the plane of the patella by the third coil.

Two resistor heaters and a plurality of freewheel diodes can be provided to the applicator. The heaters are connected in series to the femoral and tibial coils respectively. The resistor heaters and two free wheel diodes are deployed on the right and left sides of the knee. A third free wheel diode is deployed at the center of the patella. All of these heat generating elements (the three free wheel diodes and two resistive heaters) are secured on a strip formed of high thermally conductive flexible fabric that is provided to the applicator. When the applicator is wrapped around the knee during operation, the strip of heating elements delivers thermal stimulation to the treatment zone uniformly around the knee.

One of the disclosed example embodiments is a pulsed electro-magnetic field stimulation apparatus for treatment of osteoarthritis of a knee of a user. The apparatus can comprise an applicator and several coils. The applicator can include an upper part that is sized and shaped to be wrapped around a leg of the user and be located above the knee of the user, a lower part that is sized and shaped to be wrapped around the leg of the user and be located below the knee of the user, and a central part located between the upper part and the lower part such that the central part is placed on top of a patella of the user when the upper part and the lower part are both wrapped around the leg of the user.

A first coil can be provided to the upper part of the applicator such that the first coil is wrapped around the leg above the knee of the user when the upper part is wrapped around the leg of the user. A second coil can be provided to the lower part of the applicator such that the second coil is wrapped around the leg below the knee of the user when the lower part is wrapped around the leg of the user. A third coil can be provided to the central part of the applicator such that the third coil overlies the patella when the upper part and the lower part are both wrapped around the leg of the user.

The first and second coils are arranged on the applicator such that when the applicator is wrapped around the knee of the user and the first and second coils are energized, the first and second coils generate a magnetic field along the knee in a direction normal to a tibial plateau of the user. The third coil can be arranged on the applicator such that when the applicator is wrapped around the knee of the user and the third coil is energized, the third coil generates a magnetic field normal to the patella. Sequentially changing the magnetic field generated by the first and second coils provides an electric field stimulation of cartilage in a plane of the tibial plateau. Sequentially changing the magnetic field generated by the third coil provides an electric field stimulation of cartilage in a plane of the patella.

The third coil can be a flat spiral coil comprising a flexible wire.

A first resistive heater can be connected in series with the first coil and a second resistive heater can be connected in series with the second coil. Each of the first and second resistive heaters can be disposed along a respective first and second opposing sides of the knee. The first and second resistive heaters can be disposed along a strip of thermally conductive material spanning across the central part of the applicator.

A free wheel diode can be connected in series with the third coil and disposed atop the patella when the applicator is wrapped around the leg of the user. A free wheel diode can be connected in series with the first coil and another free wheel diode can be connected in series with the second coil. The free wheel diodes can be disposed along a strip of thermally conductive material spanning across the central part of the applicator. The free wheel diodes connected to the first and second coils can be disposed to opposing sides of the knee of the user when the applicator is wrapped around the leg of the user such that the third free wheel diode is disposed atop the patella.

The free wheel diode connected to the third coil can be provided in a heat sink. The heat sink can include a plurality of radial cutouts arranged to avoid eddy currents in the heat sink that would reduce the pulsed electromagnetic field in the knee of the user generated by the third coil.

A temperature sensor can be disposed adjacent to each of the free wheel diodes and or resistive heaters.

The upper part and the lower part of the applicator can each include a portion of hook and loop fastener to secure the applicator in place when wrapped around the leg of the user.

The center part of the applicator can include a thermally conductive heating patch comprising a plurality of heating elements that are arranged along a length of the heating patch.

A first cutout portion can be defined in the applicator between the upper part and the central part, and a second cutout portion can be defined between the lower part and the central part. Each of the first and second cutout portions is sized and shaped to allow for flexing of the knee while the applicator is wrapped around the leg of the user without buckling of the applicator.

The applicator can comprise a single piece of stretchable resilient fabric or it can comprise multiple pieces of fabric joined together.

In another disclosed example embodiment of a pulsed electro-magnetic field stimulation apparatus for treatment of osteoarthritis of a knee of a user, the apparatus includes an applicator configured to be wrapped around a leg of the user, and first, second and third coils provided to the applicator. The first and second coils are arranged on the applicator such that when the applicator is wrapped around the knee of the user with the third coil overlying the patella: the first coil is disposed above the knee, the second coil is disposed below the knee, when energized, the first and second coils generate a magnetic field along the knee in a direction normal to a tibial plateau of the user, when energized, the third coil generates a magnetic field normal to the patella, when sequentially changing the magnetic field generated by the first and second coils, an electric field stimulation of cartilage in a plane of the tibial plateau is provided, and when sequentially changing the magnetic field generated by the third coil, an electric field stimulation of cartilage in a plane of the patella is provided.

A first free wheel diode can be connected in series with the first coil, a second free wheel diode can be connected in series with the second coil and a third free wheel diode can be connected in series with the third coil. Each of the first, second and third free wheel diodes can be arranged on the applicator to deliver uniform heat to the knee of the user when the applicator is wrapped around the knee of the user with the third coil overlying the patella.

A first resistive heater can be connected in series with the first coil and a second resistive heater can be connected in series with the second coil. Each of the first and second resistive heaters can be disposed along a respective first and second opposing sides of the knee when the applicator is wrapped around the knee of the user with the third coil overlying the patella.

The applicator can include a thermally conductive heating patch comprising a plurality of heating elements that are arranged along a length of the heating patch to deliver uniform heat to the knee of the user when the applicator is wrapped around the knee of the user with the third coil overlying the patella.

Method of treatment and methods of operation are also provided herein.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
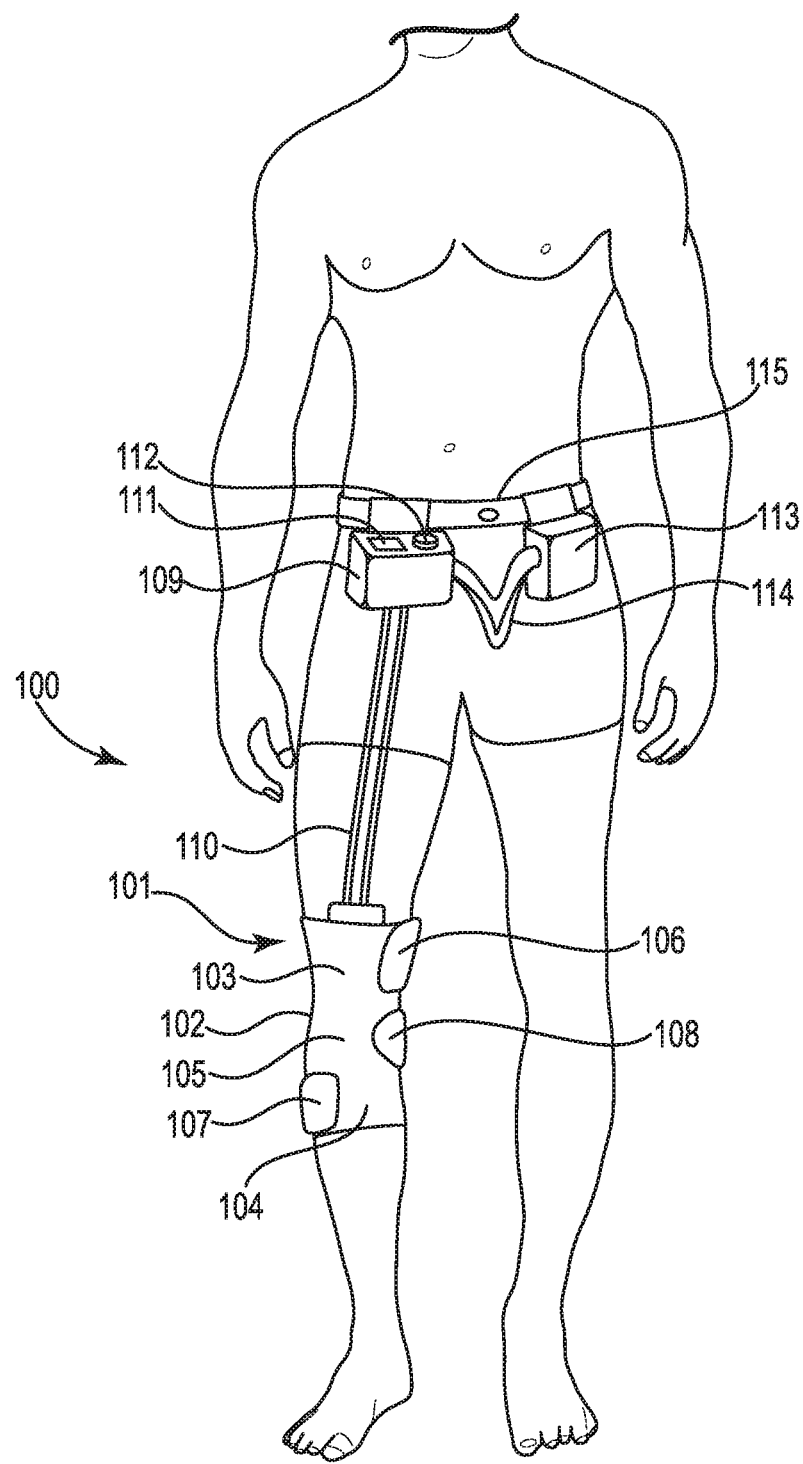
FIG. 1 is an illustration of a knee applicator wrapped around the knee of a human according to an example embodiment.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various example embodiments; nevertheless, these example embodiments are not intended to limit the present invention to any specific example, embodiment, environment, application, or particular implementation described herein. Therefore, descriptions of these example embodiments are only provided for purpose of illustration rather than to limit the present invention.

The knee, also known as the tibiofemoral joint, is a synovial hinge joint formed between three bones: the femur, tibia, and patella. Two rounded, convex processes (known as condyles) on the distal end of the femur meet two rounded, concave condyles at the proximal end of the tibia called the tibial plateau. The patella lies in front of the femur on the surface facing the femur. There are two dominant planes in the shape of the joint: vertically parallel to the patella and horizontally parallel to the tibial plateau.

The knee applicator system 100 of an example embodiment is schematically shown in FIG. 1. An applicator component 101 comprises a single piece of stretchable resilient fabric 102 that has three parts: upper part 103, lower part 104 and central part 105. The upper part 103 is wrapped around the leg above the knee and secured in this position with a hook and loop fastener (e.g. VELCRO) strap 106. The lower part 104 is wrapped around the leg below the knee and secured with a similar strap 107. The central part of the applicator 105 is placed on top of the patella and has a separate pair of fastening hook and loop fastener straps which extend transversely from both sides of the knee and meet behind the knee as shown by numeral 108. The upper 106 and lower 107 straps are separated from the central fastener 108 by a cutout portion of sufficient vertical height to allow the cutoff of fabric 102 to flex without buckling. Central fastener 108 provides necessary compression of the central part 105 to the knee which provides for adequate heat transfer from the applicator 101 to the treatment zone.

Applicator component 101 is functionally connected to computerized controller 109 via multi connector cable 110. Controller 109 includes a display 111 and an on-off button 112. Controller 109 and a power source such as a battery 113 are connected to each other with power cable 114 and secured on belt 115 which is fastened around the waist of the user. Both controller 109 and battery 113 are movably secured on belt 115 and can be shifted along it for treatment of both the right and the left knees.

Figure 2:
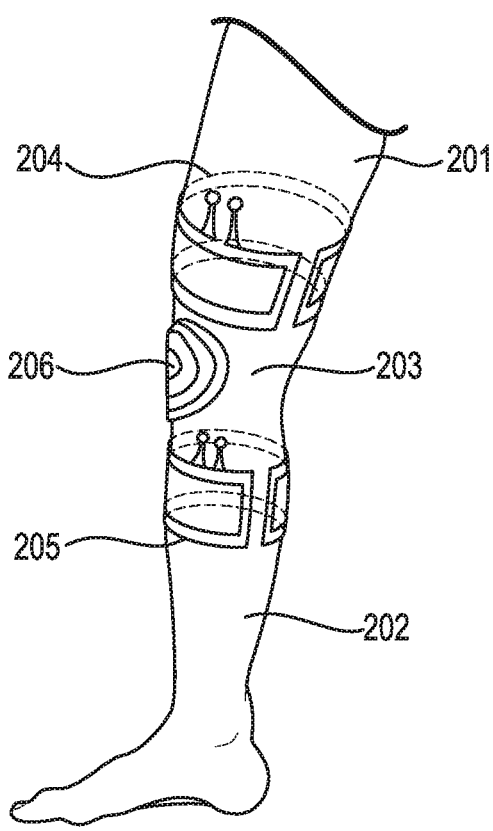
FIG. 2 is a schematic representation of the operating positions of femoral, tibial and patella coils used for treatment of the knee.

FIG. 2 schematically shows operating positions of three coils generating electromagnetic fields in the knee. Numeral 201 designates the leg above the knee, 202 below the knee and 203 the knee itself. A first coil 204 is wrapped around the leg above the knee, a second coil 205 is wrapped around the leg below the knee and coil 206 overlies the patella.

Figure 3:
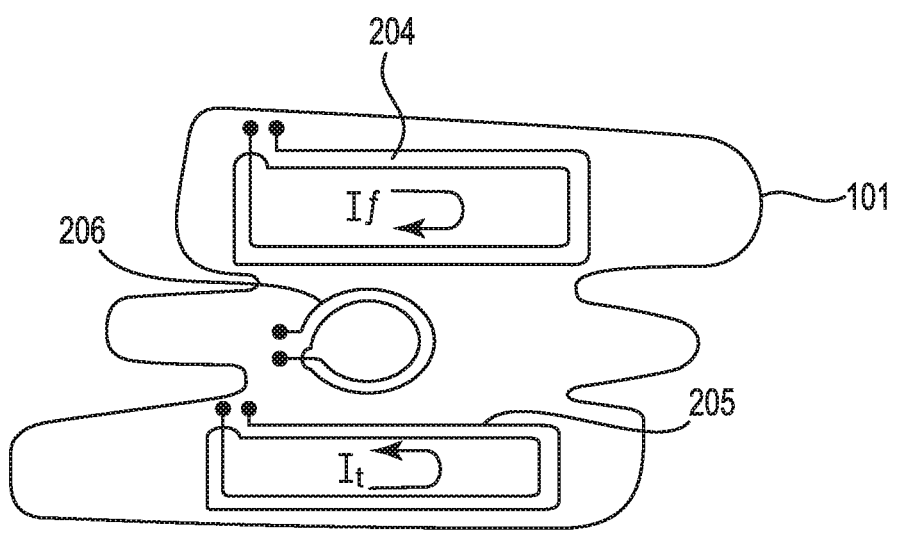
FIG. 3 is illustration of the coils in an unwrapped flat position.

FIG. 3 shows the same set of coils 204, 205, 206 in an unwrapped flat state. Coils 204 and 205 are rectangular and are formed of several turns of a very flexible wire that allows one to easily wrap them around the leg above (femoral coil) and below the knee (tibial coil) respectively. Coil 206 is a flat spiral coil (Tesla coil), also formed of a very flexible wire that allows the coil to overlie and conform to the patella and surrounding tissues of the knee. To keep their integrity, all three coils 204, 205, 206 may be imbedded in a flexible silicone compound that holds adjacent wires together.

Figures 4A, 4B:
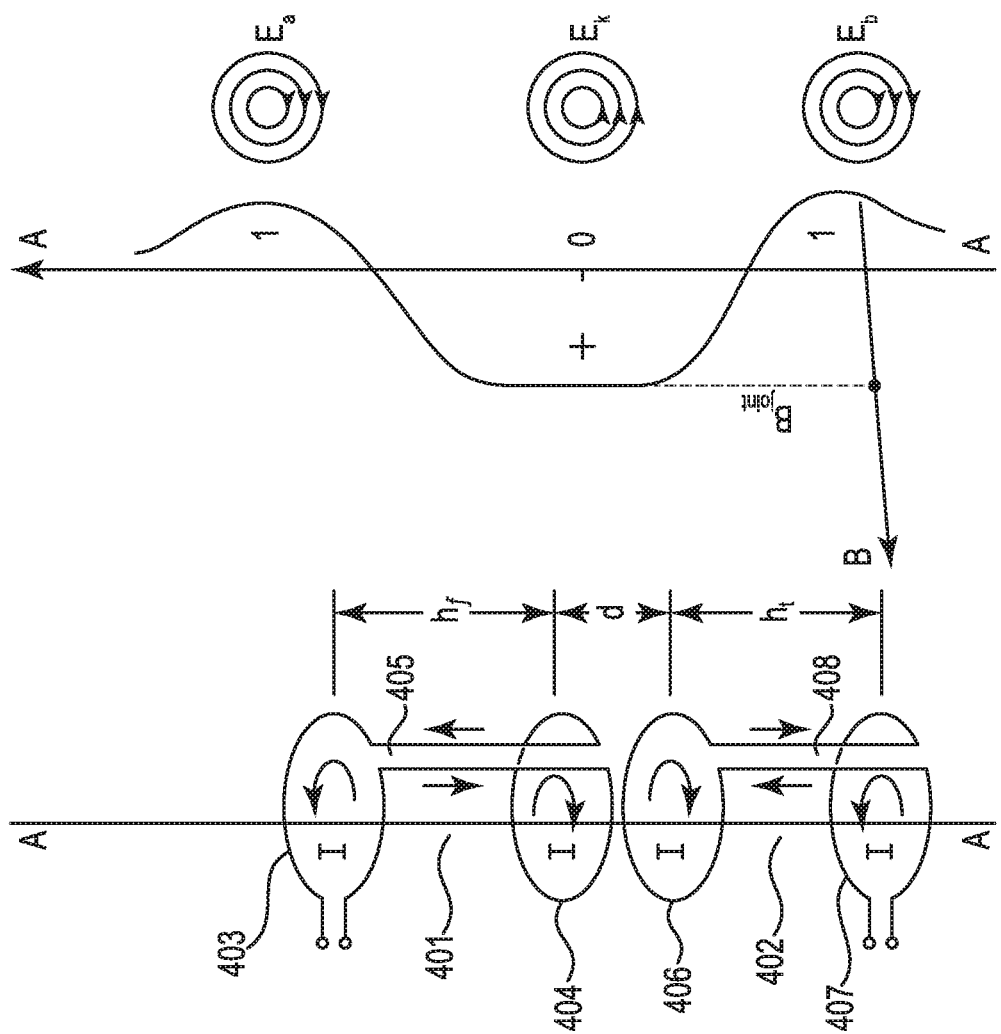
FIG. 4A schematically depicts the electric currents in the femoral and tibial coils along the axes of the knee.
FIG. 4B schematically depicts the distribution of magnetic fields created by the femoral and tibial coils along the axes of the knee.

FIG. 4A schematically depicts operational positions of coil 401 above the knee and 402 below the knee. Directions of operating currents are shown by arrows. For simplicity, the coils are shown as made of one wire only. However, in use, it is preferred to use 3 to 10 wires in each coil.

From a standpoint of generating magnetic field, coils 401 and 402 are equivalent to two loops each, the upper loop 403 and the lower loop 404 for coil 401 with two vertical wires 405 connecting loops 403 and 404. Numerals 406 and 407 designate the upper and the lower loops of the coil 402 below the knee. Numeral 408 designates a pair of vertical straight wires connecting the loops 406 and 407. Loops 403 and 404 are positioned coaxially and separated by distance $h_f$ (exemplary 5-10 cm), while loops 406 and 407 are coaxial and separated by distance $h_t$ (exemplary 5-10 cm). Diameters of the loops are defined by the sizes of the knee and the leg and are about 10-15 cm.

The most functionally important loops that create electromagnetic field in the treatment zone of the knee are loops 404 and 406. These loops are positioned adjacent to each other with separation distance "d" between them of about 3-5 cm longitudinally across the knee. These loops carry electric current in the same direction. Coils 404 and 406 generate magnetic field along the axis A-A and electric field in the plane normal to axis A-A.

The two parallel vertical pairs of wires 405 and 408 in a wrapped state are positioned in close proximity to each other. Each pair carries identical electric currents in opposite directions and thus generates magnetic fields that offset each other. Thus the effects of their magnetic and electric fields are negligible.

FIG. 4B shows a graph of magnetic inductance B along the axis of the knee A-A and lines of electric field $E_k$ in the knee area, and above and below the knee areas $E_a$ and $E_b$ respectively. In the knee area, magnetic field is generated by loops 404 and 406 and reaches values of about 10-20 mT. The electric field in the treatment zone reaches a value of about 10-20 mV/cm. The vector of magnetic field is directed along the axis of the loops normally to the tibial plateau and the cartilage layer that covers it.

When the magnetic field between loops 404 and 406 changes, a circular electric field in the knee cartilage layers is generated parallel to the tibial plateau. At the distances from the knee $h_f$ and $h_t$, loops 403 and 407 create magnetic fields of the opposite direction to the magnetic field in the knee. Loops 403 and 407 generate the magnetic fields at the knee area that are subtracted from the field created by loops 404 and 406 at the knee and thus decrease the magnetic field in the treatment area. But, as calculations show, the negative contribution of the loops 403 and 407 to the magnetic field in the knee area is less than 10% of the field generated by loops 404 and 406 located near the knee. Loops 403 and 407 generate magnetic and electric fields far above and below the treatment area, where the tissues are healthy. These loops do not create any side effects because of the well-known fact that PEMF does not have any significant biological effects on the healthy tissues, because they have low concentration of free adenosine.

Previous devices in the art created magnetic field in the knee via a simple solenoid wound around the knee. Such prior design of PEMF applicator for the treatment of the knee required pulling a patient's foot through a knee sleeve on which the solenoid is secured and further pulling the sleeve over the knee. These maneuvers were not simple and convenient, and particularly so for many patients such as elderly or overweight people. In contrast, the present design of the PEMF applicator provided herein can advantageously be wrapped up around the knee with minimal effort and used for treatment.

Figure 5:
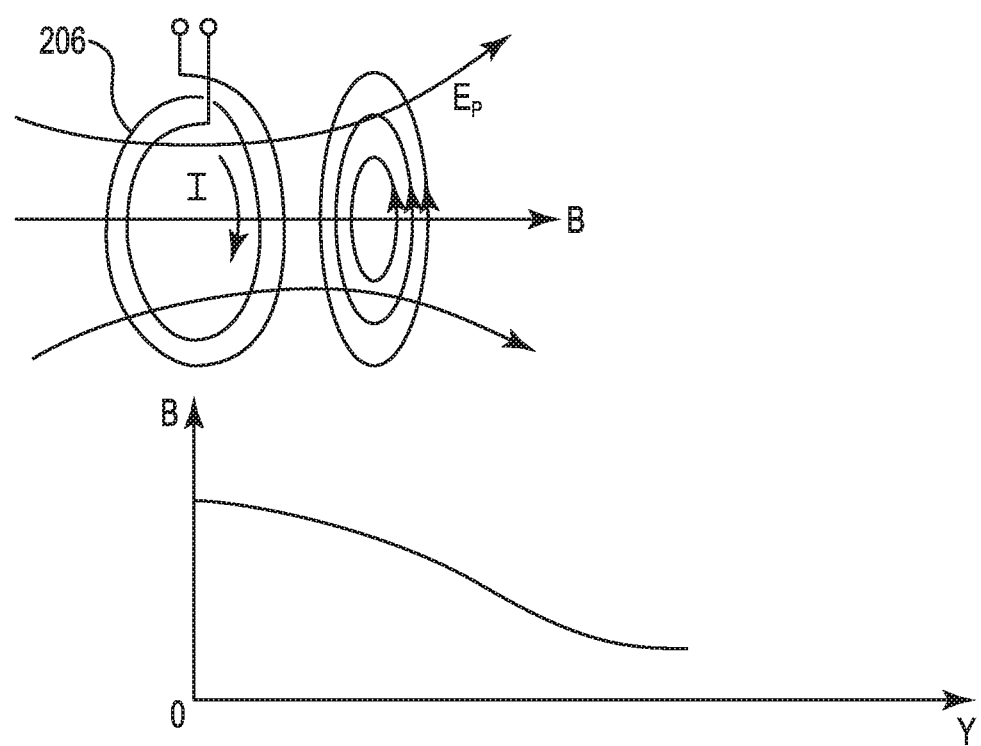
FIG. 5 schematically depicts the electric current and magnetic field in the patella coil along its axis adjacent to a schematic depiction of the distribution of the magnetic field created by the patella coil along its axis.

FIG. 5 schematically shows coil 206 and the distribution of the amplitude of the magnetic field along the axis of the patella coil 206. Also, the diagram illustrates electric field at the patella area. Magnetic field in the patella area is about 15-20 mT, while the circular electric field is about 15-20 mV/cm.

Figure 6:
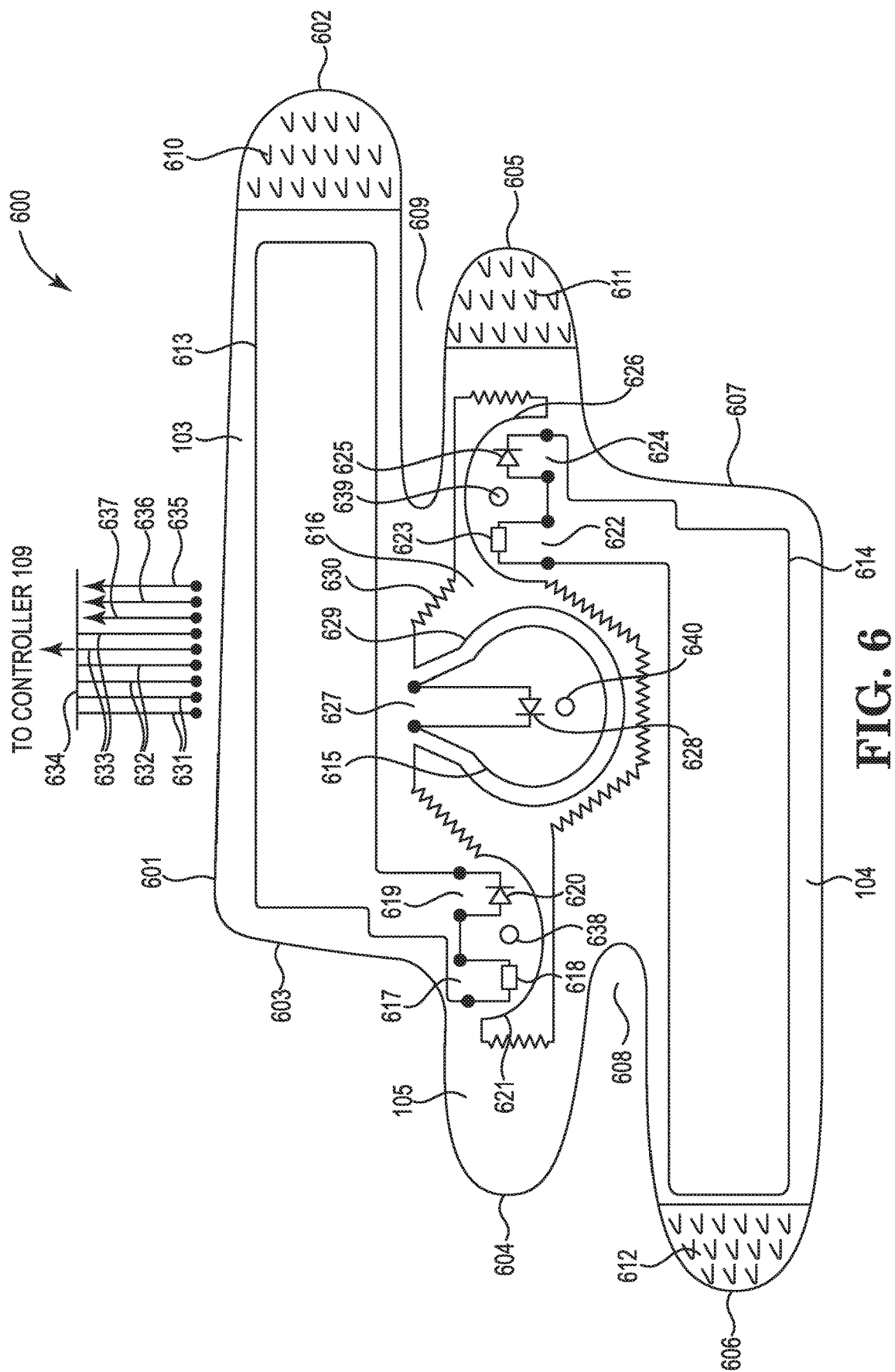
FIG. 6 schematically shows a posterior view of the knee applicator according to an example embodiment.

The posterior view of knee applicator 600 is schematically shown in FIG. 6. The applicator 600 is shown in its unwrapped state without an inside layer of soft fabric that covers the applicator 600 from the side surface that faces the knee. Numeral 601 designates a single piece of flexible resilient fabric that comprises three parts: an upper part 103, a lower part 104 and central part 105 and serves as a basis for securing all major electronic and thermal parts of the applicator. These parts correspond with the numerical part designation in FIG. 1

The upper part 103 is intended to be wrapped around the user's leg above their knee. The right and left ends 602 and 603 of the upper part 103 are locked with VELCRO or other hook-and-loop fastener 610. The lower part 104 is wrapped around the user's leg below the knee and ends 606 and 607 are locked together with a hook and loop tab fastener 612 and free end 607. In a similar manner the central part 105 of the basic piece 601 can be locked around the user's knee at the patella level.

Deep cutouts 608 and 609 formed in the basic piece 601 allow for independent fastening of all three parts 103, 104, 105 of the applicator 600 without buckling. Tabs 610, 611 and 612 carry arrays of hook-and-loop type fasteners.

The significance of a three-part design of the applicator 600 is in its ability to independently select its vertical position by using the upper and lower fastener tabs 610, 612, and to adjust compression of the central part of the applicator 600 to the knee using central fastener tab 611 independently from two other fasteners 610, 612. Also, deep cutouts 608 and 609 above and below the knee allow the user to walk relatively freely during a treatment session.

In order to create magnetic field normal to the vertical plane that is parallel to the patella and the horizontal plane that is parallel to the tibial plateau there are two sources of the magnetic field provided in applicator 600. Coil 613, secured on the upper part 103 of the applicator and coil 614 secured on the lower part 104 of the applicator are powered synchronously and generate magnetic field normally to the tibial plateau. When the magnetic fields of coils 613 and 614 change, they generate a circular electric field in the plane of tibial plateau and the articular cartilage parallel to the plateau. When the magnetic field in coil 615 changes it generates a circular electric field in the plane of the patella to stimulate the articular cartilage of the patella and articular cartilages of the femur and the tibia parallel to the patella.

An elongated strip or patch 616 of flexible fabric material that has high thermal conductivity stretches along a central part 105 of applicator 600. In a wrapped state the fabric material encircles the knee and serves as a heat bridge for heat transfer from the elements of the applicator that generate heat to the treatment zone of the knee. The upper coil 613 via contacts 617 is connected in series with resistive heater 618 and via contacts 619 with free wheel diode 620 schematically shown in cutout 621 in the patch 616. Similarly, lower coil 614 via contacts 622 is connected in series with resistive heater 623 and via contacts 624 with free wheel diode 625 schematically shown in cutout 626. Patella coil 615 via contacts 627 is connected in series with free wheel diode 628, schematically shown in cutout 629.

Central patch 616 is sewn to central part 105 of the applicator 600 with a stretchable seam 630. All three free wheel diodes 620, 625, 628 used in the applicator 600 are high current Schottky diodes that are used for circuit protection from high voltage spikes during a turning off of the electrical current.

Coils 613, 614 and 615 via contacts 619, 624 and 627, respectively, are connected with wires (not shown) to three pairs of high current wires 631, 632 and 633 that connect applicator 600 with a controller 109 of the system. Three pairs of low current double wires 635, 636 and 637 connect three thermal sensors 638, 639 and 640 provided to the applicator with the temperature stabilization system of controller 109.

Figure 7:
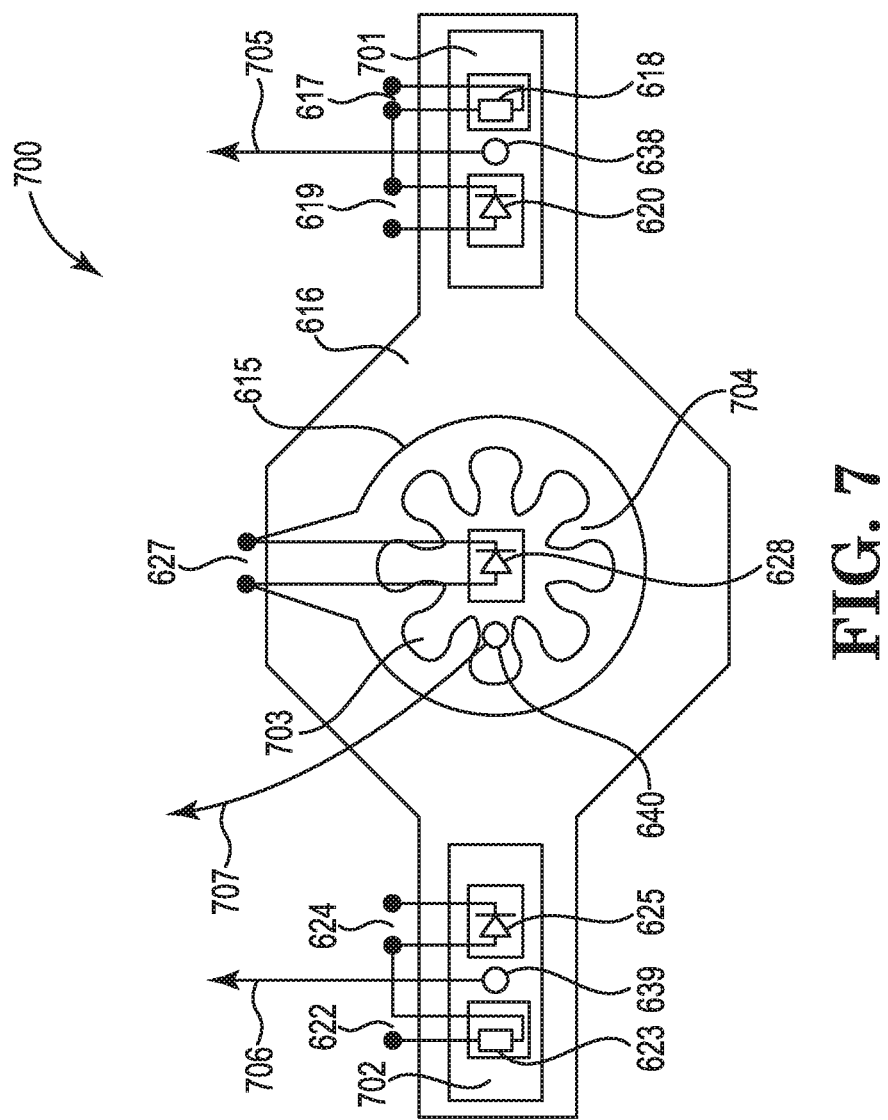
FIG. 7 shows an anterior view of the electronic assembly of the applicator secured on a patch of thermally conductive fabric.

FIG. 7 shows a front view of the patch assembly 700. The assembly 700 includes patch 616 formed of flexible material with high thermal conductivity, preferably carbon fiber fabric. Central coil 615, for simplicity shown as having only one turn, is secured at the center of patch 616. Central coil 615 via contacts 627 is connected to free-wheel Schottky diode 628. Contacts 627 are also connected to high current wires 633 of multi wire cable 634, leading to controller 109 (connecting wires are not shown). Similarly, free wheel diodes 620 and 625 via contacts 619 and 624 are connected to high current wires 631 and 632 of multi wire cable 634 respectively.

Schottky free wheel diode 628 is secured on heat sink 703. The heat sink 703 is formed from a round piece of flexible copper foil that provides cooling for the diode 628 and heating for patch 616 which, in turn, transfers the heat to the patella. Copper foil heat sink 703 has a plurality of radial cutouts 704 formed to avoid excessive eddy currents in the foil that can reduce pulsed electromagnetic field in the treatment zone generated by coil 615. Schottky free wheel diodes 620 and 625 are connected to coils 613 and 614 respectively.

Resistive heater 618 is connected to coil 613 in series via contacts 617. The resistive heater 623 is connected to the coil 614 in series via contacts 622. Both resistive heaters 618, 623 have resistance in the range of tens of milliohms, which is several times higher than the resistance of coils 613 and 614. This leads to preferential deposition of magnetic energy of the coils 613, 614 into the resistive heaters 618, 623.

Heater 618 and free wheel diode 620 are secured on the flexible copper foil 701 that is secured on the thermally conductive patch 616. The copper foil 701 serves as a heat sink for diode 620 and as a heater for the thermally conductive patch 616. The thermally conductive patch 616 transfers heat generated by the free wheel diode 620 and the heater 618 to the treatment zone of the knee.

Heater 623 and free wheel diode 625 are secured on the flexible copper foil 702 that is secured on the thermally conductive patch 616. Copper foil 702 serves as a heat sink for diode 625 and a heater for the thermally conductive patch 616. The thermally conductive patch 616 transfers heat generated by free wheel diode 625 and heater 623 to the treatment zone of the knee.

Numerals 638, 639 and 640 designate temperature sensors secured on heat sinks 701, 702 and 703. Low current double wires 705, 706 and 707 connect the respective thermal sensors to low current double wires 635, 636 and 637 of the multi wire cable 634 leading to controller 109.

In use the patch 616 is wrapped approximately in a 270-degree arc around the knee. Using the hook and loop fastener 611 tab of the central part 105 of the applicator 600, the user can select compression of thermally conductive heating patch 616 to the knee. This arrangement provides an adequate and adjustable thermal contact of the central part 105 of the applicator 600 and the treatment zone of the knee.

Figure 8:
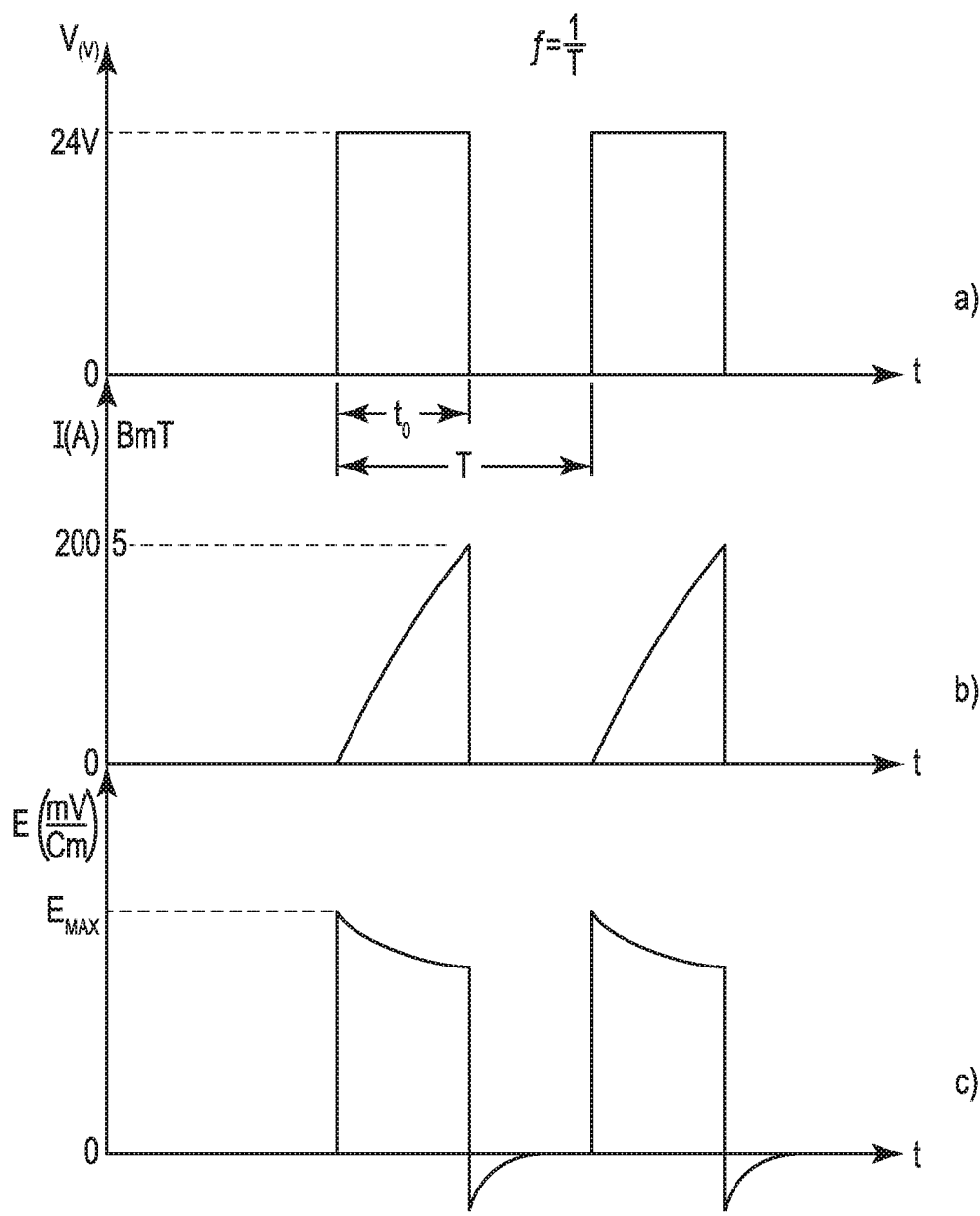
FIG. 8 provides three time diagrams depicting the voltage, current, magnetic field and stimulation electric field generated by each coil.

The controller 109 supplies coils 613, 614 and 615 with rectangular DC pulses such as shown in FIG. 8, diagram a). The preferred amplitude of the pulses is 24 V. Duration of the pulses $t_0$ may be in the range of 10-100 microseconds, and the time interval between pulses T is in a range of 4 to 200 milliseconds, which corresponds to frequency (repetition rate) range 5 to 250 Hz.

As a parameter of pulsing, frequency is used for temperature stabilization of the treatment zone. An operating frequency depends on the deviation of actual temperature in the treatment zone from the temperature selected by the user. If actual temperature is too low, the frequency is increased to deliver an increased amount of thermal energy to the treatment zone, and the treatment zone temperature will increase as a result. If actual temperature of the treatment zone is too high, then the frequency will be decreased so that the thermal energy delivered to the treatment zone decreases, and the temperature of the treatment zone will decrease as a result. In other words, the temperature of the treatment zone is stabilized at the level selected by the user by means of controlling operational frequency.

FIG. 8, diagram b) shows an exemplary graph of electric current I in the coils and proportional to it the magnetic induction B, both as functions of time. The peak current is about 200-300 A, and the peak of magnetic induction is in the range of 5-10 mT.

The electric field in the treatment zone is shown in FIG. 8, diagram c). The amplitude of electric field pulses "Emax" is about 15-20 mV/cm.

It is also within the scope of the invention to combine features, functions, advantages and aspects of the various embodiments described herein. Thus the embodiments of the invention may comprise combinations of aspects of any one or more of these exemplary embodiments.

While the invention has been described in connection with what is presently considered to be the most practical and preferred example embodiments, it will be apparent to those of ordinary skill in the art that the invention is not to be limited to the disclosed example embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. A pulsed electro-magnetic field (PEMF) stimulation apparatus for treatment of osteoarthritis of a knee of a user, the apparatus comprising:
   an applicator, comprising:
      an upper part that is sized and shaped to be wrapped around a leg of the user and be located above the knee of the user;
      a lower part that is sized and shaped to be wrapped around the leg of the user and be located below the knee of the user; and
      a central part located between the upper part and the lower part such that the central part is placed on top of a patella of the user when the upper part and the lower part are both wrapped around the leg of the user;
   a first multi-turn rectangular coil comprising an upper horizontal side, a lower horizontal side, a left vertical side and a right vertical side, the first multi-turn rectangular coil provided to the upper part of the applicator such that each of the upper horizontal side and the lower horizontal side are wrapped around at least a majority of a circumference of the leg above the knee of the user and such that the upper horizontal side is positioned to create a loop above the knee outside a treatment zone of the knee while the lower horizontal side is positioned to create a loop in the treatment zone adjacent to an upper part of the knee when the upper part of the applicator is wrapped around the leg of the user;
   a second multi-turn rectangular coil comprising an upper horizontal side, a lower horizontal side, a left vertical side and a right vertical side, the second multi-turn rectangular coil provided to the lower part of the applicator such that each of the upper horizontal side and the lower horizontal side are wrapped around at least a majority of the circumference of the leg below the knee of the user and such that the lower horizontal side is positioned to create a loop below the knee outside the treatment zone of the knee while the upper horizontal side is positioned to create a loop in the treatment zone adjacent to a lower part of the knee when the lower part of the applicator is wrapped around the leg of the user;
   a third coil provided to the central part of the applicator such that the third coil overlies the patella when the upper part and the lower part are both wrapped around the leg of the user, wherein the first and second coils are arranged on the applicator such that when the applicator is wrapped around the knee of the user and the first and second coils are energized, the first and second coils generate a magnetic field along the knee in a direction normal to a tibial plateau of the user, wherein the third coil is arranged on the applicator such that when the applicator is wrapped around the knee of the user and the third coil is energized, the third coil generates a magnetic field normal to the patella, wherein synchronously changing the magnetic field generated by the first and second coils provides an electric field stimulation of cartilage in a plane of the tibial plateau, and wherein sequentially changing the magnetic field generated by the third coil provides an electric field stimulation of cartilage in a plane of the patella.

2. The apparatus of claim 1, wherein the third coil is a flat spiral coil comprising a flexible wire.

3. The apparatus of claim 1, further comprising a first resistive heater connected in series with the first coil and a second resistive heater connected in series with the second coil, wherein each of the first and second resistive heaters are disposed along a respective first and second opposing sides of the knee.

4. The apparatus of claim 3, further comprising a free wheel diode connected in series with the third coil and disposed atop the patella when the applicator is wrapped around the leg of the user.

5. The apparatus of claim 3, further comprising a first free wheel diode connected in series with the first coil and a second free wheel diode connected in series with the second coil.

6. The apparatus of claim 3, wherein the first and second resistive heaters are disposed along a strip of thermally conductive material spanning across the central part of the applicator.

7. The apparatus of claim 1, further comprising a first free wheel diode connected in series with the first coil, a second free wheel diode connected in series with the second coil and a third free wheel diode connected in series with the third coil.

8. The apparatus of claim 7, wherein the first, second and third free wheel diodes are disposed along a strip of thermally conductive material spanning across the central part of the applicator.

9. The apparatus of claim 7, wherein the first and second free wheel diodes are disposed to opposing sides of the knee of the user when the applicator is wrapped around the leg of the user such that the third free wheel diode is disposed atop the patella.

10. The apparatus of claim 7, wherein the third free wheel diode is provided in a heat sink, the heat sink including a plurality of radial cutouts arranged to avoid eddy currents in the heat sink that would reduce the pulsed electromagnetic field in the knee of the user generated by the third coil.

11. The apparatus of claim 7, further comprising a first temperature sensor disposed adjacent to the first free wheel diode, a second temperature sensor disposed adjacent to the second free wheel diode and a third temperature sensor disposed adjacent to the third free wheel diode.

12. The apparatus of claim 7, further comprising a first resistive heater connected in series with the first coil and a second resistive heater connected in series with the second coil, wherein each of the first and second resistive heaters are disposed along the center part of the applicator.

13. The apparatus of claim 1, wherein the upper part and the lower part each include a portion of hook and loop fastener to secure the applicator in place when wrapped around the leg of the user.

14. The apparatus of claim 1, wherein the central part includes a thermally conductive heating patch comprising a plurality of heating elements that are arranged along a length of the heating patch.

15. The apparatus of claim 1, wherein a first cutout portion is defined between the upper part and the central part, and a second cutout portion is defined between the lower part and the central part, each of the first and second cutout portions sized and shaped to allow for flexing of the knee while the applicator is wrapped around the leg of the user without buckling of the applicator.

16. The apparatus of claim 15, wherein the center part defines a portion of hook and loop fastener between the first and second cutout portions to secure the applicator in place when wrapped around the leg of the user.

17. The apparatus of claim 1, wherein the applicator comprises a single piece of stretchable resilient fabric.

18. A PEMF stimulation apparatus for treatment of osteoarthritis of a knee of a user, the apparatus comprising:
an applicator configured to be wrapped around a leg of the user;
a first multi-turn rectangular coil provided to the applicator;
a second multi-turn rectangular coil provided to the applicator; and
a third coil provided to the applicator,
wherein the first and second multi-turn rectangular coils are arranged on the applicator such that when the applicator is wrapped around the knee of the user with the third coil overlying the patella:
the first coil is disposed above the knee such that when the applicator is wrapped around the leg of the user, the first coil defines an upper loop and a lower loop around the leg of the user,
the second coil is disposed below the knee such that when the applicator is wrapped around the leg of the user, the second coil defines an upper loop and a lower loop around the leg of the user,
when energized, the lower loop of the first coil and the upper loop of the second coil synchronously generate a magnetic field along the knee in a common direction normal to a tibial plateau of the user,
when energized, the lower loop of the first coil generates a magnetic field in a first direction while the upper loop of the first coil generates a magnetic field in a second direction that is opposite of the first direction,
when energized, the upper loop of the second coil generates a magnetic field in a first direction while the lower loop of the second coil generates a magnetic field in a second direction that is opposite of the first direction,
when energized, the third coil generates a magnetic field normal to the patella,
when synchronously changing the magnetic field generated by the first and second coils, an electric field stimulation of cartilage in a plane of the tibial plateau is provided, and
when sequentially changing the magnetic field generated by the third coil, an electric field stimulation of cartilage in a plane of the patella is provided.

19. The apparatus of claim 18, further comprising a first free wheel diode connected in series with the first coil, a second free wheel diode connected in series with the second coil and a third free wheel diode connected in series with the third coil, wherein each of the first, second and third free wheel diodes are arranged on the applicator to deliver uniform heat to the knee of the user when the applicator is wrapped around the knee of the user with the third coil overlying the patella.

20. The apparatus of claim 18, further comprising a first resistive heater connected in series with the first coil and a second resistive heater connected in series with the second coil, wherein each of the first and second resistive heaters are disposed along a respective first and second opposing sides of the knee when the applicator is wrapped around the knee of the user with the third coil overlying the patella.

21. The apparatus of claim 18, wherein the applicator includes a thermally conductive heating patch comprising a plurality of heating elements that are arranged along a length of the heating patch to deliver uniform heat to the knee of the user when the applicator is wrapped around the knee of the user with the third coil overlying the patella.

\* \* \* \* \*